(12) United States Patent
Birchard et al.

(10) Patent No.: US 8,603,046 B2
(45) Date of Patent: Dec. 10, 2013

(54) AUTOMATED INJECTION CATHETER DEVICE AND SYSTEM

(75) Inventors: Christopher J. Birchard, Pasadena, CA (US); Jerett A. Creed, Hermosa Beach, CA (US); Wai Chung Jonathan Wong, Chino Hills, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 1175 days.

(21) Appl. No.: 12/125,893

(22) Filed: May 22, 2008

(65) Prior Publication Data

US 2009/0099514 A1    Apr. 16, 2009

Related U.S. Application Data

(60) Provisional application No. 60/939,649, filed on May 23, 2007.

(51) Int. Cl.
A61M 5/00    (2006.01)

(52) U.S. Cl.
USPC .......................................................... 604/235

(58) Field of Classification Search
USPC .................................. 604/95.01, 156, 159, 235
See application file for complete search history.

(56) References Cited

U.S. PATENT DOCUMENTS

| | | | |
|---|---|---|---|
| 3,605,742 A * | 9/1971 | Tibbs ............................ | 604/112 |
| 3,941,130 A * | 3/1976 | Tibbs ............................ | 604/136 |
| 4,108,177 A * | 8/1978 | Pistor ............................ | 604/155 |
| 4,228,802 A | 10/1980 | Trott | |
| 4,391,199 A | 7/1983 | Morin | |
| 5,176,647 A | 1/1993 | Knoepfler | |
| 5,217,441 A | 6/1993 | Shichman | |
| 5,380,292 A | 1/1995 | Wilson | |
| 5,478,316 A * | 12/1995 | Bitdinger et al. ............. | 604/135 |
| 5,480,387 A | 1/1996 | Gabriel et al. | |
| 5,688,243 A | 11/1997 | Rammler | |
| 5,938,603 A | 8/1999 | Ponzi | |
| 5,997,509 A | 12/1999 | Rosengart et al. | |
| 6,123,699 A | 9/2000 | Webster, Jr. | |

(Continued)

FOREIGN PATENT DOCUMENTS

| WO | WO 99/59663 | 11/1999 |
|---|---|---|
| WO | WO 02/30554 A2 | 4/2002 |

(Continued)

OTHER PUBLICATIONS

International Search Report, dated Aug. 27, 2008 for corresponding International Application No. PCT/US2008/064667, 4 sheets, indicating relevance of listed references on this IDS.

(Continued)

*Primary Examiner* — Theodore Stigell
*Assistant Examiner* — Diva K Chander
(74) *Attorney, Agent, or Firm* — Christie, Parker & Hale, LLP (57) ABSTRACT

A device and system for automating catheter needle injection has a first actuator that extends a needle past the distal end of the catheter, a second actuator that depresses a plunger to deliver injectate through the needle and an agitator assembly to agitate the injectate before it enters the needle. The device and system may also include a force sensor coupled to the plunger to sense pressure to detect occlusion, and an optical sensor to sense movement of the second actuator.

16 Claims, 8 Drawing Sheets

(56) References Cited

U.S. PATENT DOCUMENTS

| | | | |
|---|---|---|---|
| 6,165,164 A * | 12/2000 | Hill et al. | 604/523 |
| 6,171,277 B1 | 1/2001 | Ponzi | |
| 6,183,463 B1 | 2/2001 | Webster, Jr. | |
| 6,201,387 B1 | 3/2001 | Govari | |
| 6,254,573 B1 * | 7/2001 | Haim et al. | 604/157 |
| 6,309,370 B1 | 10/2001 | Haim et al. | |
| 6,321,106 B1 | 11/2001 | Lemelson | |
| 6,385,472 B1 | 5/2002 | Hall et al. | |
| 6,484,118 B1 | 11/2002 | Govari | |
| 6,540,725 B1 | 4/2003 | Ponzi | |
| 6,575,931 B1 | 6/2003 | Ponzi | |
| 6,623,474 B1 | 9/2003 | Ponzi | |
| 6,802,824 B2 * | 10/2004 | Mickley et al. | 604/164.12 |
| 6,980,843 B2 | 12/2005 | Eng et al. | |
| 7,300,438 B2 | 11/2007 | Falwell et al. | |
| 7,399,294 B2 | 7/2008 | Mickley | |
| 8,079,982 B1 | 12/2011 | Ponzi et al. | |
| 2003/0117888 A1 | 6/2003 | Reilly et al. | |
| 2003/0195491 A1 | 10/2003 | Schneider et al. | |
| 2003/0233076 A1 * | 12/2003 | Mickley et al. | 604/246 |
| 2004/0039338 A1 | 2/2004 | Lee et al. | |
| 2004/0204672 A1 | 10/2004 | Palasis et al. | |
| 2005/0038390 A1 * | 2/2005 | Fago et al. | 604/187 |
| 2005/0234337 A1 * | 10/2005 | Browne | 600/432 |
| 2009/0018497 A1 | 1/2009 | Birchard et al. | |
| 2009/0099513 A1 | 4/2009 | Birchard et al. | |
| 2009/0099514 A1 * | 4/2009 | Birchard et al. | 604/95.01 |

FOREIGN PATENT DOCUMENTS

| | | |
|---|---|---|
| WO | WO 2004/014533 A1 | 2/2004 |
| WO | WO 2005/077441 A2 | 8/2005 |
| WO | WO 2005077441 A2 * | 8/2005 |

OTHER PUBLICATIONS

International Search Report dated Sep. 5, 2008 for International Application No. PCT/US2008/064652 (7 pages).

International Search Report dated Sep. 8, 2008 for International Application No. PCT/US2008/064661 (6 pages).

* cited by examiner

AUTOMATED INJECTION CATHETER DEVICE AND SYSTEM

CROSS-REFERENCE TO RELATED APPLICATION(S)

This application claims priority to U.S. Provisional Application No. 60/939,649, filed May 23, 2007, the entire disclosure of which is hereby incorporated by reference.

FIELD OF INVENTION

The present invention relates to injection catheters, and in particular to injection catheter systems.

BACKGROUND

Electrode catheters have been in common use in medical practice for many years. They have been used to stimulate and map electrical activity in the heart and to ablate sites of aberrant electrical activity. More recently, therapeutic and diagnostic agents have been delivered into the heart, including the heart wall, also through a percutaneous transluminal approach with the use of injection catheters. In particular, catheters with a needle have been used for injection directly into the myocardium for a variety of treatments, including myocardial revascularization. For example, U.S. Pat. No. 6,309,370 entitled Intracardiac Drug Delivery, the entire disclosure of which is hereby incorporated by reference, is directed methods and apparatuses to provide accurate minimally-invasive methods and apparatus for intracardiac administration of drugs to the myocardium.

In use, the electrode catheter is inserted into a major vein or artery, e.g., femoral artery, and then guided into the chamber of the heart of concern. Under conventional procedures, navigation of the catheter to the target site is accomplished by a physician operating a deflection control handle aided by fluoroscopy of the heart region. And, while the physician manually controls and maintains the position of the catheter at the tissue target site, another staff member is needed to operate a separate needle control handle for injecting the needle into tissue and delivering therapeutic agent through the lumen of the injection needle. Such needle control handles are described in U.S. Pat. No. 6,575,931 (Ponzi) and U.S. Pat. No. 6,623,474 (Ponzi). In these needle control handles, a cylinder and piston arrangement is provided to extend the needle past the catheter distal tip to penetrate tissue and a syringe is provided to deliver the therapeutic agents. While such needle control handles are very effective, the consistency and accuracy of needle penetration and injection can be as varied as the visual and manual acuity of the different physicians or assistants operating the needle control handle. Indeed, people have different hand strengths and each person calibrates differently, not to mention the differences even with the very same person from one instance to the next. Thus, the consistency and accuracy in the use of needle control handles for tissue penetration and delivery of therapeutic agents, particularly in terms of injection volume and injection rate, can be improved upon.

Moreover, in recent years, remote (remote magnetic technology (RMT)) and robotic manipulation of catheters have been used for mapping and other procedures. These remotely guided catheters allow for more automation with improved accuracy and efficiency in the maneuvering and positioning of catheters reducing the dependence of success based upon the physical dexterity and physician manipulation manual skill. And, by enabling navigation from a location remote from patient, these catheters have also greatly reduced, if not eliminated, the physician's exposure to fluoroscopic radiation. However, while remote catheters obviate the use of manual deflection control handles, the needle control handle has continued under conventional design to be tethered to the proximal end of the catheter body and thus still near the patient. Thus, it would be desirable that the needle control handle be automated to obviate the need for a needle control assistant to control needle extension, injection and retraction.

Accordingly, it is desirable to provide device and system for automating needle control, including the extension and retraction of the needle and the actuation of the syringe for greater consistency and accuracy in use, including needle penetration, injection volume and injection rate. It is also desirable for the device and system to allow the use of larger syringes so that a single syringe can provide the volume of therapeutic agents called for in current clinical procedures. It is further desirable for the device and system to provide agitation of the therapeutic agents carried in the syringe to minimize settling and coagulation. It is yet further desirable for the device and system to detect occlusion or other possible malfunctions so that actuation of the syringe does not occur until tissue penetration has been achieved, and actuation of the syringe is interrupted if an occlusion is detected.

SUMMARY OF THE INVENTION

The present invention is directed to a device that automates operation of an injection catheter by providing a first actuator adapted to extend a needle of the injection catheter, and a second actuator adapted to deliver injectate through the needle and out its distal end. The device may also include an agitator assembly to agitate the injectate and a force sensor to detect occlusion in the needle.

In one embodiment, the device acts on a catheter needle injector having a piston assembly and a syringe with a plunger, the device having a first actuator that compresses the piston assembly, a second actuator that depresses the plunger, and a rotation assembly adapted to rotate the syringe to minimize settling and coagulation of injectate in the syringe. The device may also include a force sensor coupled to the plunger to sense pressure in the syringe to detect occlusion, and an optical sensor to sense movement of the second actuator.

In another embodiment, the device includes a first actuator assembly having a movable support member coupled thereto for extending the needle, and a second actuator assembly that is adapted to move with the movable support member for delivery the injectate through the needle while the needle is extended. An agitator assembly, including an electric actuator acting on rotation levers and arms, or a motor driven gear system, to rotate the syringe, may also be adapted to move with the movable support.

The device provides a housing that effectively seals the first and second actuators and rotation assembly for sanitation and sterilization purposes while enabling components to reach the catheter injector outside the housing. Moreover, the device is compact due to space-saving arrangements of the first and second actuators within the housing.

The present invention in another embodiment also includes a system having a catheter injection automation device that is responsive to a computer having a CPU, a display and a user input to actuate the device to extend the needle, deliver therapeutic agents through the needle and retract the needle. The system also enables user input to control the agitator system and the rate at which agitation occurs. The system further enables a user to set the rate of injection and to retract the needle in stages.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
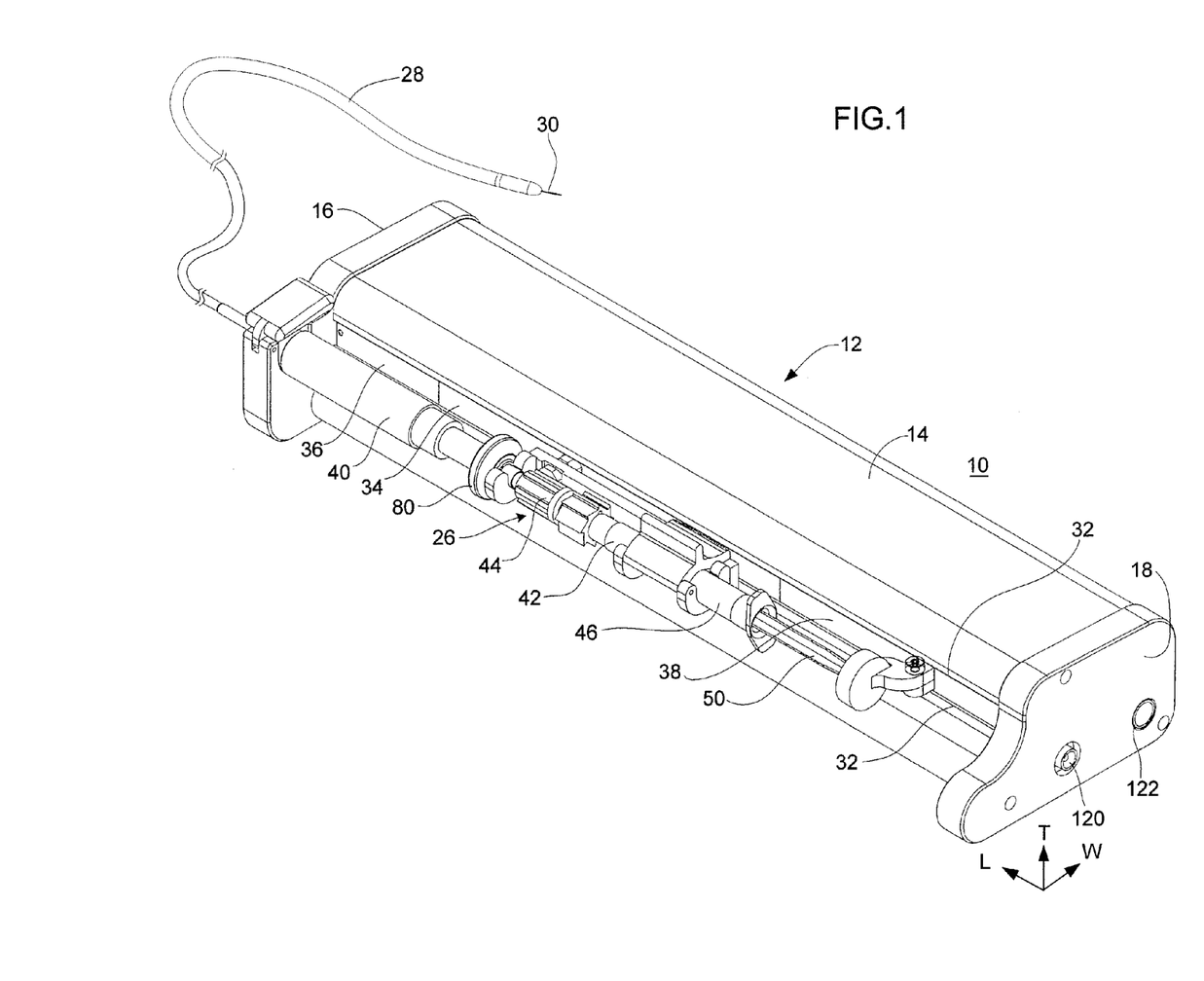
FIG. 1 is a perspective of an embodiment of a device for automating catheter needle injection with an injector, in accordance with the present invention.
Figure 2:
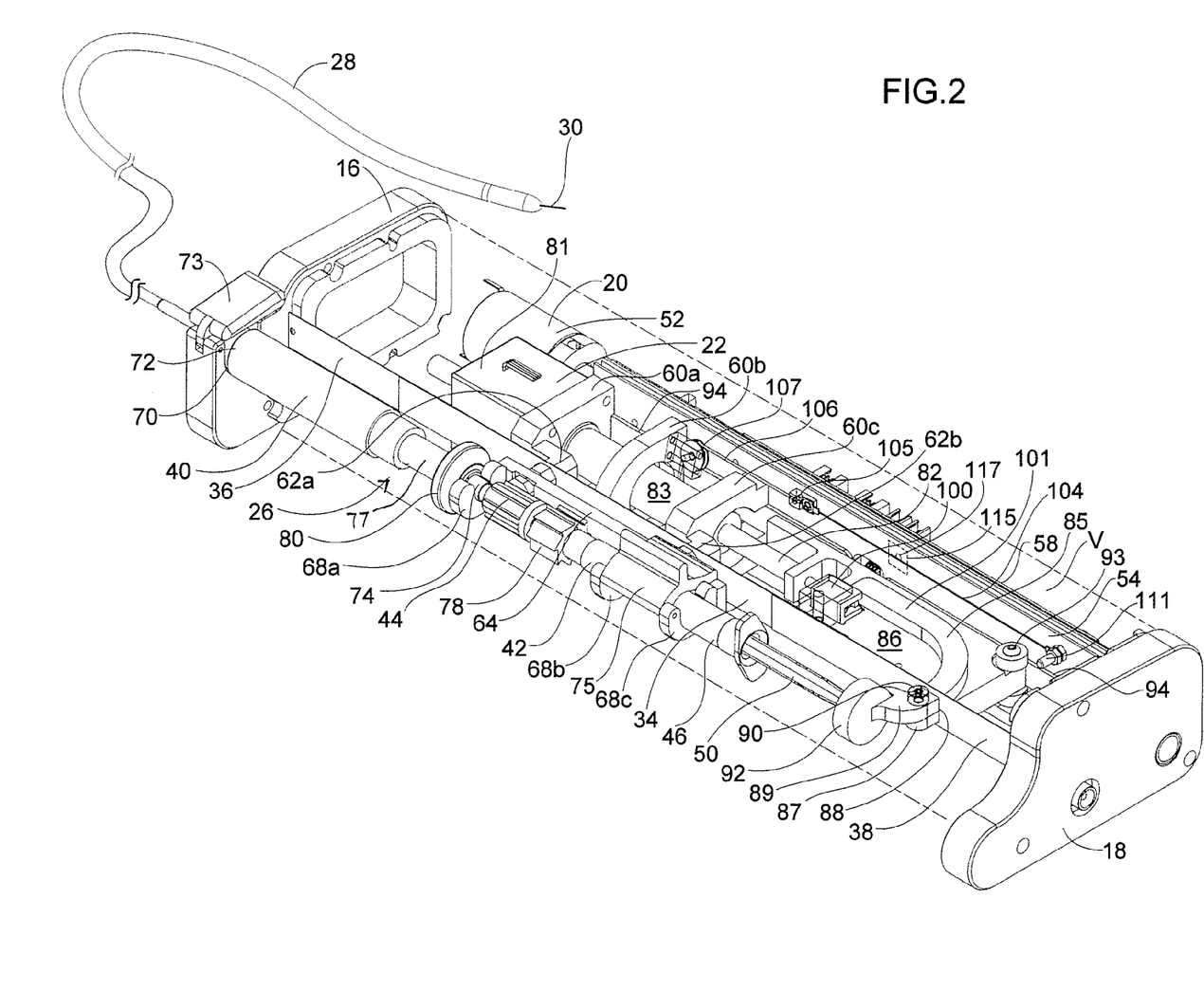
FIG. 2 is a perspective of the device of FIG. 1, with an outer shell of a housing removed to reveal the interior.

With reference to FIGS. 1 and 2, an embodiment of a device 10 for automating catheter needle injection of therapeutic agents, includes a housing 12 with an enclosed, multi-sided volume V that is defined by an extruded outer shell 14, a distal end cap 16 and a proximal end cap 18. The housing encloses various components including a needle control assembly 20, an injection control assembly 22, and an agitator assembly 24. The device 10 also includes a needle injector (or needle control handle) 26 which is supported outside of the housing. Distal the needle injector is a catheter 28 adapted for insertion into a major vein or artery, e.g., femoral artery, and then guided into the heart. Extending through the catheter is an injection needle 30 whose proximal end terminates in the injector 26 and whose distal end can extend past the distal end of the catheter 28. The catheter is equipped for remote navigation but a manually deflected catheter is also suitable for use with the device 10.

The outer shell 14 is continuous with a wrap-around extruded configuration such that two edges 32 oppose each other on a common side of the volume and are separated by a longitudinal gap. Advantageously, the enclosed volume V occupies the majority of the device, thereby limiting the number of structures outside of the enclosed volume. Although the injector 26 is supported proximally to the gap between the edges 32 and actuated by structures that extend through the gap from the enclosed volume, communication between the volume and outside environment is significantly minimized by an elongated panel 34, a distal shield 36 and a proximal shield 38 that protect the enclosed volume and seal the gap except for various openings in the panel 34 and shield 38 through which the structures extend. Thus, for sanitation and sterilization purposes, the housing presents a readily-accessible exterior surface to clean. Only exposed components need sterilization while the assemblies, parts and components in the enclosed volume remain isolated from the environment and vice versa. A removable and sterilizable soft cover (not shown) over the housing can further isolate the enclosed volume.

The device 10 has a generally rectangular shape with a length L defining a longitudinal direction, a width W and a thickness T, the combination of which gives the device a generally sleek and compact configuration and appearance. As the device is intended to occupy minimal space and be used in proximity of the patient, it is advantageous for the device to present an unobtrusive and inconspicuous appearance. The length L ranges between about 8 and 20 inches, preferably about 9 and 15 inches, and more preferably about 10 and 12 inches. The width W ranges between about 4 and 10 inches, preferably about 5 and 8 inches, and more preferably about 4 and 5 inches. The thickness T ranges between about ½ and 8 inches, preferably about 1 and 4 inches, and more preferably about 2 and 3 inches.

In the illustrated embodiment, the needle injector 26 has an assembly similar to needle control handles disclosed in U.S. Pat. No. 6,575,931 (Ponzi) and U.S. Pat. No. 6,623,474 (Ponzi), the entire disclosures of which are hereby incorporated by reference. The injector 26 has a piston assembly 40 (having an outer body or cylinder 27 and a piston 29), a syringe 42 distal thereof, and a luer 44 rotatably coupling the assembly and the syringe. The piston assembly 40 compresses (that is, the piston is moved distally relative to the cylinder) under a longitudinal force in the distal direction to extend the injection needle 30 past the distal end of the catheter. The piston assembly 40 includes a spring coil (not shown) distal of the piston which returns the piston to its original resting position upon removal of the longitudinal force. The syringe 42 includes a barrel 46 containing injectate and a depressible plunger 50. Thus, each instance or cycle of injection involves compression of the piston assembly 40 to extend the needle, depression of the plunger for delivery of the therapeutic agent into tissue, and release of the piston assembly 40 to retract the needle.

Figures 3, 3A:
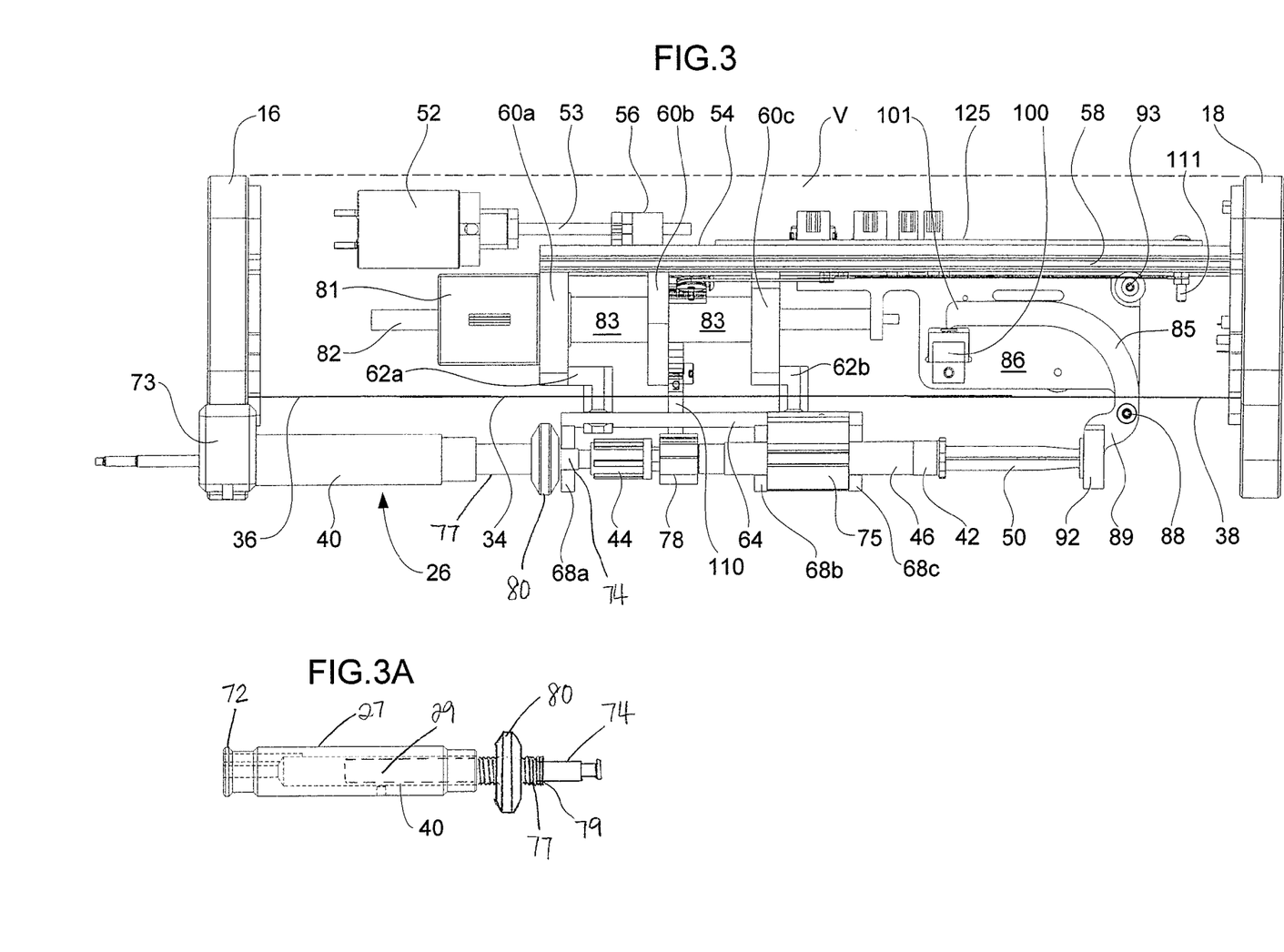
FIG. 3 is a top plan view of the device of FIG. 2.
FIG. 3a is a side elevational view of an embodiment of a piston assembly having a cylinder and a piston.

With reference to FIGS. 2 and 3, the needle control assembly 20 in the enclosed volume serves to compress the piston assembly 40. The needle control assembly includes a linear actuator, a translatable support member, and various mounting and support brackets. In the illustrated embodiment, the linear actuator is a motor (e.g., a 52 Maxon REMax 24 mm motor (222049)) and a lead screw 53, and the translatable support member includes an elongated guide plate 54 that is coupled to the lead screw by bracket 56. The guide plate translates in the longitudinal direction of the housing under control of the motor 52. In particular, as the motor draws the lead screw in, the guide plate is drawn distally. In that regard, upper and lower edges of the guide plate have a recessed track 58 that engages a linear ridge (not shown) formed in inner upper and lower walls of the extruded shell 14 to guide the longitudinal translation of the guide plate in the proximal and distal directions.

Mounted to the guide plate are transverse mounting brackets 60a, 60b and 60c, with arms 62a and 62b, respectively, that extend through the openings in the elongated gap panel 34. Supported by the arms outside of the housing is a bar 64 that extends longitudinally alongside the elongated panel. Extending from the bar are multiple snap-fit, C-shaped brackets 68a, 68b and 68c to hold the injector 26.

A distal end of the injector 26 is supported in a recess 70 formed in the extended portion of the distal end cap 16. The distal end of the injector has an outer ring 72 (FIG. 3a) that sits in a groove in the recess. When latch 73 is secured, the distal end of the piston assembly is effectively immobilized against movement in the distal and proximal directions. Proximal portions of the injector including a luer hub 74 of the piston assembly and the barrel 46 of the syringe are cradled in the brackets 68a, 68b and 68c. A wider threaded portion 77 distal the luer hub 74 provides a ring formation 79 which a distal surface of the bracket 68a abuts. Latch 75 secures the barrel in the proximal pair of brackets 68b and 68c such that movement of these brackets directly imparts movement to the proximal portion of injector 26 against the immobilized distal end of the piston assembly 40. With actuation of the motor 52, the needle control assembly applies a longitudinal force on the proximal portion of the injector 26 sufficient to compress the piston assembly 40 and extend the needle 30 for tissue penetration. It is understood that successful tissue penetration involves multiple factors including the speed and force with which the threaded portion 77 (and hence the piston) is driven distally relative to the cylinder of assembly 40. Because the injector 26 allows for a user's manual adjustment of the throw or extension distance of the needle, namely, by means of knob 80, the motor 52 has a clutch release mechanism to disengage the motor when the throw is less than the maximum extension distance possible with the injector.

Notably, the distal-most C-shaped bracket 68a is configured to hold the injector 26 at the junction of the luer hub 74 and a flat distal most section of threaded portion 77, proximal of the adjustment knob 80. The ring formation 29 provides a suitable surface on which the bracket 68a acts to drive the piston into the cylinder of the assembly 40. Moreover, in accordance with a feature of the present invention, the injector 26 is consistently and securely held in a predetermined position relative to the device 10 for needle extension. It is understood that whereas the adjustment knob 80 is movable by a user, the threaded portion 77 is not. Notably, while the injector 26 is secured in the brackets 68, the syringe 42 still has rotational freedom from the piston assembly 40 by means of the rotatable luer 44 that is received in the luer hub 74. In that regard, the rotatable luer includes a drive ratchet 78 proximal of its rotatable adapter. The rotatable adapter allows 360 rotational freedom between the piston assembly and the syringe. The drive ratchet however is directly coupled to the distal end of the syringe such that rotation of the drive ratchet causes rotation of the syringe, the significance of which is discussed further below.

The needle control assembly 22 (also referred to as a plunger actuation assembly) housed in the enclosed volume V serves to depress the plunger 50. In the illustrated embodiment, the assembly 22 includes a motorized linear actuator 81 (e.g., Haydon Switch actuator, part number 28H47-12-925ENG) and a shaft 82 driven by the actuator. The actuator 81 is mounted to the mounting bracket 60a which has an opening to accommodate an extended portion 83 of the actuator which extends through openings in the mounting brackets 60b and 60c. As a space saving measure, the assembly 22 includes a force translating member so that the actuator 81 can be angularly offset from the plunger 50. In the disclosed embodiment, the force translating member is a curved or J-shaped lever arm 85 that is coupled to a proximal end of the shaft 82 by means of a linear extension plate 86 which allows the actuator 81 to be about 180 degrees offset and generally parallel with the injector 26 and plunger 50. The extension plate 86 has a stub 87 that extends through opening 88 in the proximal shield 38 along with an end 89 of the lever arm 85. The lever arm 85 is pivotally coupled to the plate 86 at the stub by means of a pin 90. The exposed end of the lever arm outside the enclosed volume has a contact pad 92 configured to contact and abut a distal end of the plunger 50. With activation of the linear actuator 81, the shaft 82 is drawn distally to act on the lever arm 85 as coupled by the extension plate 86 and the pin 88. The plunger 50 is depressed by the contact pad 92 to deliver the therapeutic agent through the lumen of the needle 30 in the catheter 28. The extension plate 86 at a proximal corner opposing the stub and pin has a pair of bearings 93 whose movement is guided by a ledge 94 defined along an inwardly-facing surface of the guide plate 54 of the needle control assembly 20.

The device include includes detection means for detecting occlusion. In the illustrated embodiment, a force sensor 100 is responsive to pressure from opposing end 101 of the lever arm 85. The force sensor is bound by parameters defining an upper control limit or forces greater than those achieved during injection into tissue thereby indicating occlusion. As the contact pad 92 presses on the plunger 50, changes in pressure in the syringe 42 cause slight pivoting of the lever arm 85 about the pin 90 which are detected by the force sensor 100. As such, the force sensor may be able to detect occlusion along the lumen of the injection needle 30 or absence or loss of tissue penetration. For example, an initial rise in pressure followed by a slow decrease during injection may indicate successful delivery of injectate into tissue, whereas no changes in pressure may indicate an absence or loss of tissue penetration. The force sensor is integrated within the device 10 to sense occlusions in the needle lumen and emergency stop injection cycles.

Notably, the entirety of the plunger actuation assembly 22 is supported on the guide plate 54 to move in unison with the needle control assembly 20. Since needle extension requires compression of the piston assembly 40 by means of a distal shifting of the rotatable luer 44 and the syringe 42, and injection is intended to occur only while the needle 30 is extended, the plunger actuation assembly necessarily moves with the rotatable luer and the syringe. This movement in unison is effectively enabled by the guide plate 54 to which the mounting brackets 60a, 60b, and 60c are connected and on which the bearings 93 of the extension plate 86 travel. Being affixed to the arms 62 of the mounting brackets 60, the elongated panel 34 advantageously moves with the plunger actuation assembly 22, which in turn moves with the guide plate 54 under the control of the needle control assembly 20. The elongated panel 34 is of a sufficient length that its distal and proximal ends remain overlapped with the distal and proximal shields 36 and 38 throughout an injection cycle. Accordingly, the gap between edges 32 of the shell remains sealed throughout operation of the device.

Figure 4:
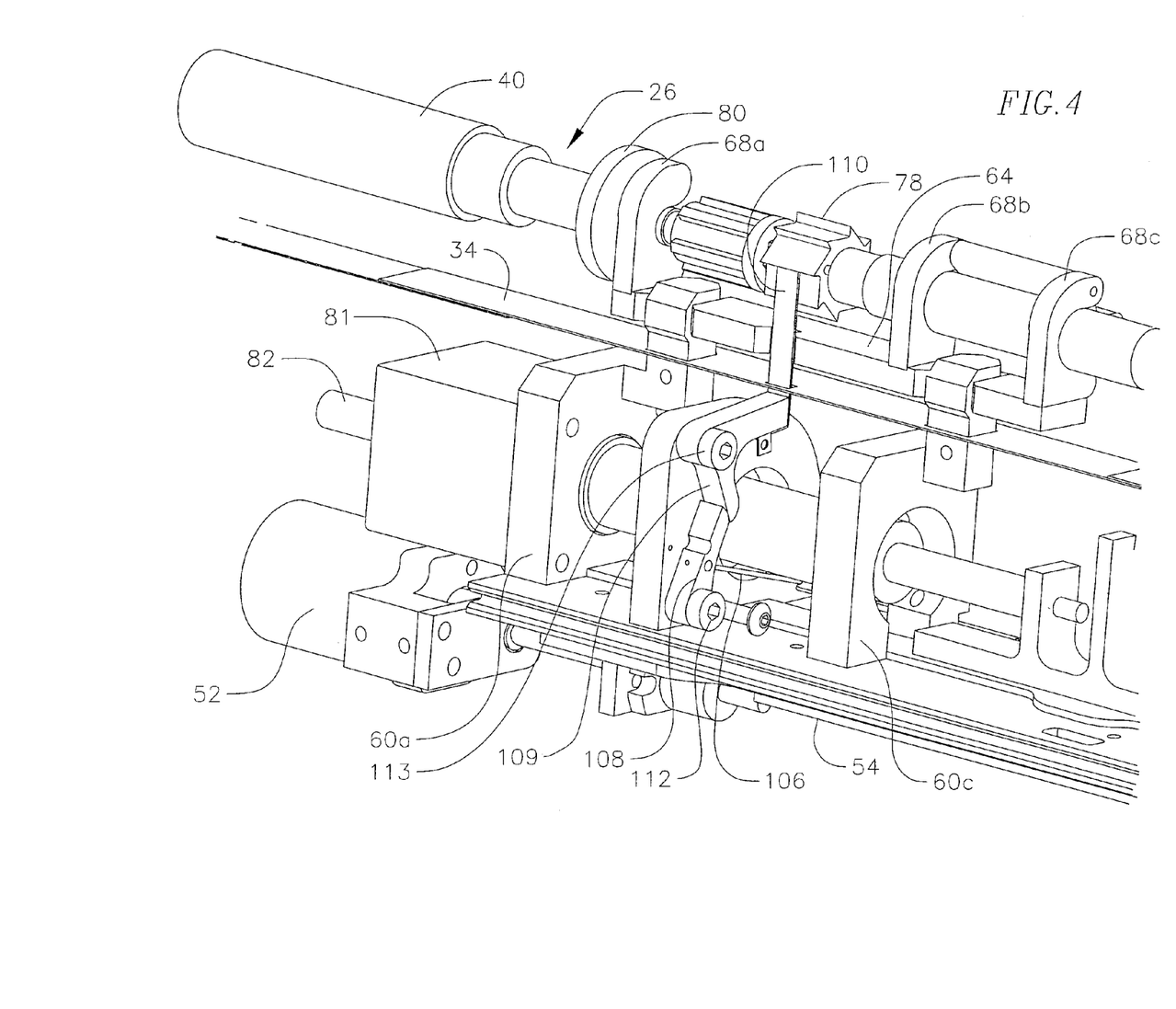
FIG. 4 is a partial bottom view of the device of FIG. 2., including an embodiment of an agitator assembly.

Conventional therapeutic agents include solutions that can settle over time. Thus, the device also includes means for agitating the injectate contained in the barrel of the syringe. In the disclosed embodiment, the agitator assembly 24 includes an electric actuator and a rotation assembly that act on the drive ratchet 78 on the injector 26 to rotate the syringe 42. In the illustrated embodiment of FIG. 4, the electric actuator includes a predetermined length of nitinol wire 104 that contracts to a predetermined contracted length when heated. The nitinol wire is connected at one end by a clamp 105 to one end of a nonelastic tensile extender 106 (e.g., extension wire) that engages a pulley 107 which redirects the extender under the linear actuator 81. Referring to FIGS. 3 and 4, the rotation assembly has a rotation lever 108 and a rotation arm 109 with a rotation pusher 110 that extends through an opening in the elongated panel 34 to act on the drive ratchet 78 on the injector 26.

An electrical current is passed through the nitinol wire from a PC board 125 via anchor bolt 111. A lead wire (not shown) attached to the nitinol wire near the connector clamp 105 and proximal of the pulley 107 completes the circuit back to the PC board. As the current passes through the nitinol wire 104, the nitinol wire heats up due to resistive heating and contracts to the predetermined contracted length which draws the tensile extender 106 to rotate the rotation lever 108 about a shoulder bolt 112. The rotation (clockwise in FIG. 4) brings the rotation lever into engagement with the rotation arm 109 which rotates the latter (counter-clockwise in FIG. 4) about shoulder bolt 113 which extends the rotation pusher 110. As the pusher 110 extends, it pushes a gear on the ratchet 78 and rotates the ratchet 78 to turn the syringe 42.

As the nitinol wire 104 cools, it is returned to its unheated length by a spring return (not shown) provided, for example, in the rotation lever 108 which biases the rotation lever (counterclockwise in FIG. 4) to apply tension on the extender 106 and lengthen the nitinol wire 104 from its contracted state. The rotation arm 109 may also be biased by a spring return (not shown) to rotate (clockwise in FIG. 4) when it is released by the rotation lever 118. Upon release, the arm 109 rotates drawing the pusher 110 back which puts it in position to push another ratchet when the nitinol is heated again. In this manner, the injectate in the syringe is agitated whenever the nitinol wire is energized.

Figure 4A:
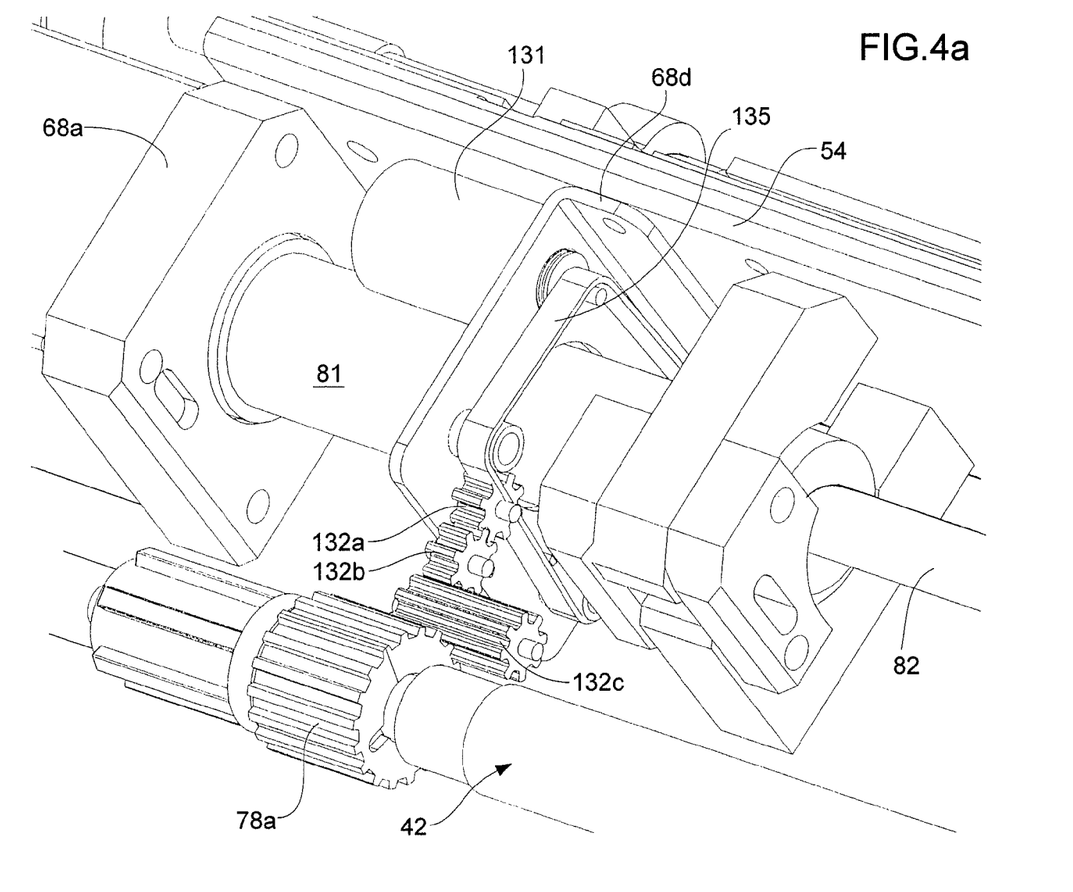
FIG. 4a is a partial top view of an alternate embodiment of the device, including an alternate embodiment of an agitator assembly, with various surrounding components not shown.

The agitator assembly 24 in another embodiment as illustrated in FIG. 4a includes a driven gear assembly mounted on a mounting bracket 60d (in lieu of bracket 60b) that is affixed to the guide plate 54. The driven gear assembly include a rotation motor 131 coupled to a gear assembly 133 by a belt 135 notched with openings to engage gear teeth. As the motor is actuated, the belt is driven to rotate gear 133a which in turn rotates gears 133b and 133c, the latter of which is engaged with a gear 78a mounted on the rotatable luer thus rotating the syringe 42. In this manner, the injectate in the syringe is agitated whenever the motor 131 is actuated.

In another alternate embodiment, the injectate can also be agitated by means of an orbital shaker platform 141 that supports the device 10 and moves the device in its entirety. It is understood that such platforms can move in a variety of patterns, including orbital, rocking, reciprocating, figure-eight, shaking, and clockwise and counterclockwise motions. In yet another alternate embodiment, one or more magnetic elements are disposed in the barrel of the syringe and move in response to an external magnet or electromagnet which is activated intermittently to agitate the injectate.

The device may also include verification means to confirm movement of the plunger assembly 22. Such means may include an optical reader 115 (FIG. 2) mounted on the PC board 125 behind an opening 117 in the guide plate 54 which allows sensing of an optically-readable indicator (not shown) (e.g., a reflective bar code) affixed to an opposing surface of the extension plate 86. So arranged, the optical reader travels with the guide plate and is situated to sense movement of the extension plate 86 by reading the indicator. The optical reader provides delivery feed back and verification to validate movement of the shaft of the plunger actuation assembly 22. Where the actuator 81 moves a set distance at a given rate under the control of the user, the optical reader serves to confirm or deny the accomplishment of that task. In the latter instance, there may exist an occlusion any where along the length of the needle or some other mechanical failure of the plunger actuation system 22. It also accounts for potential mechanical loss within the workings of the components of the device. Linear distances requested are achieved by rotational actuation where mechanical loss of ideal movement would occur, for example, with treads of the screw drive, angular displacement of the lever arm, etc. The optical reader is a redundant verification of linear movement.

Figure 5:
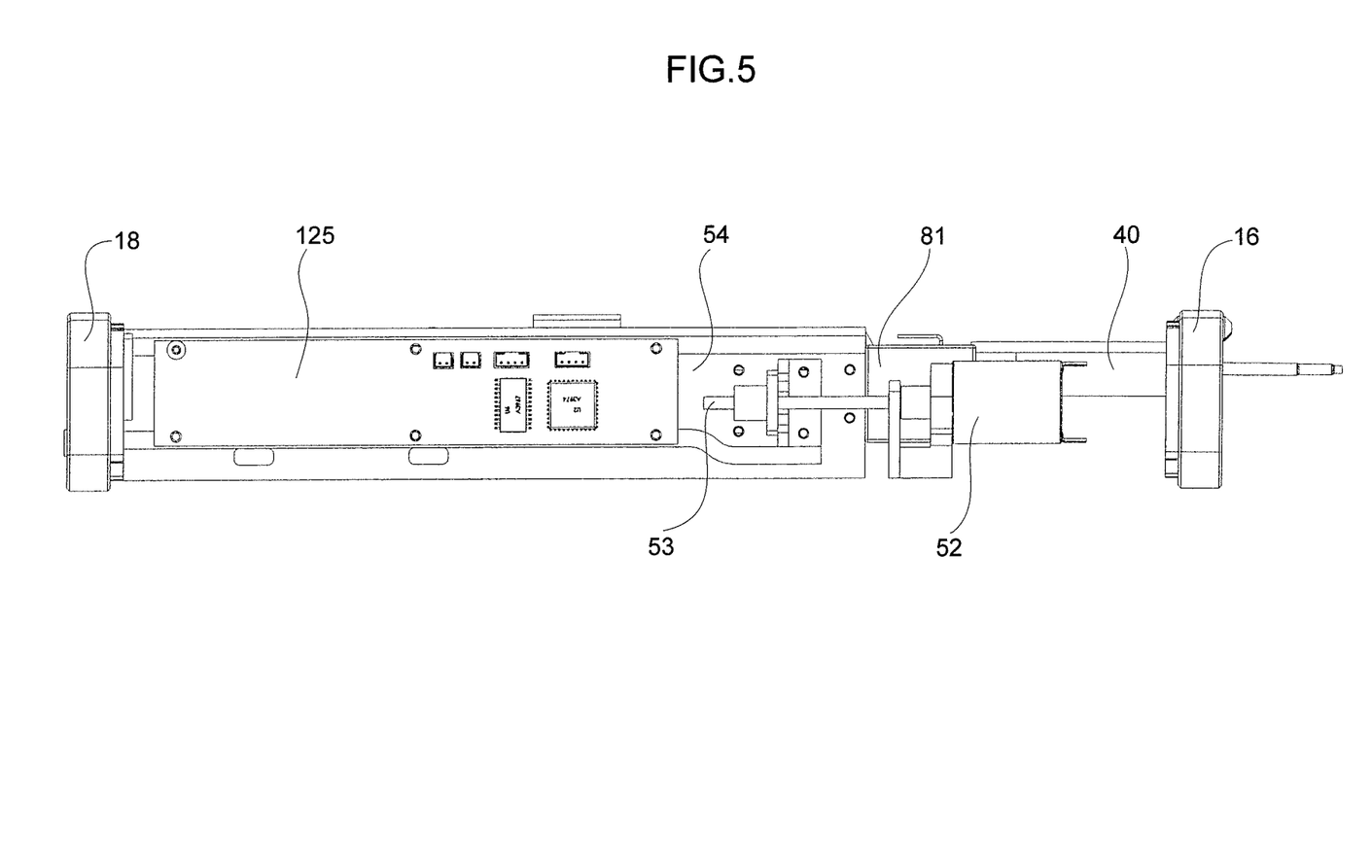
FIG. 5 is an elevated back view of the device of FIG. 2.
Figure 7:
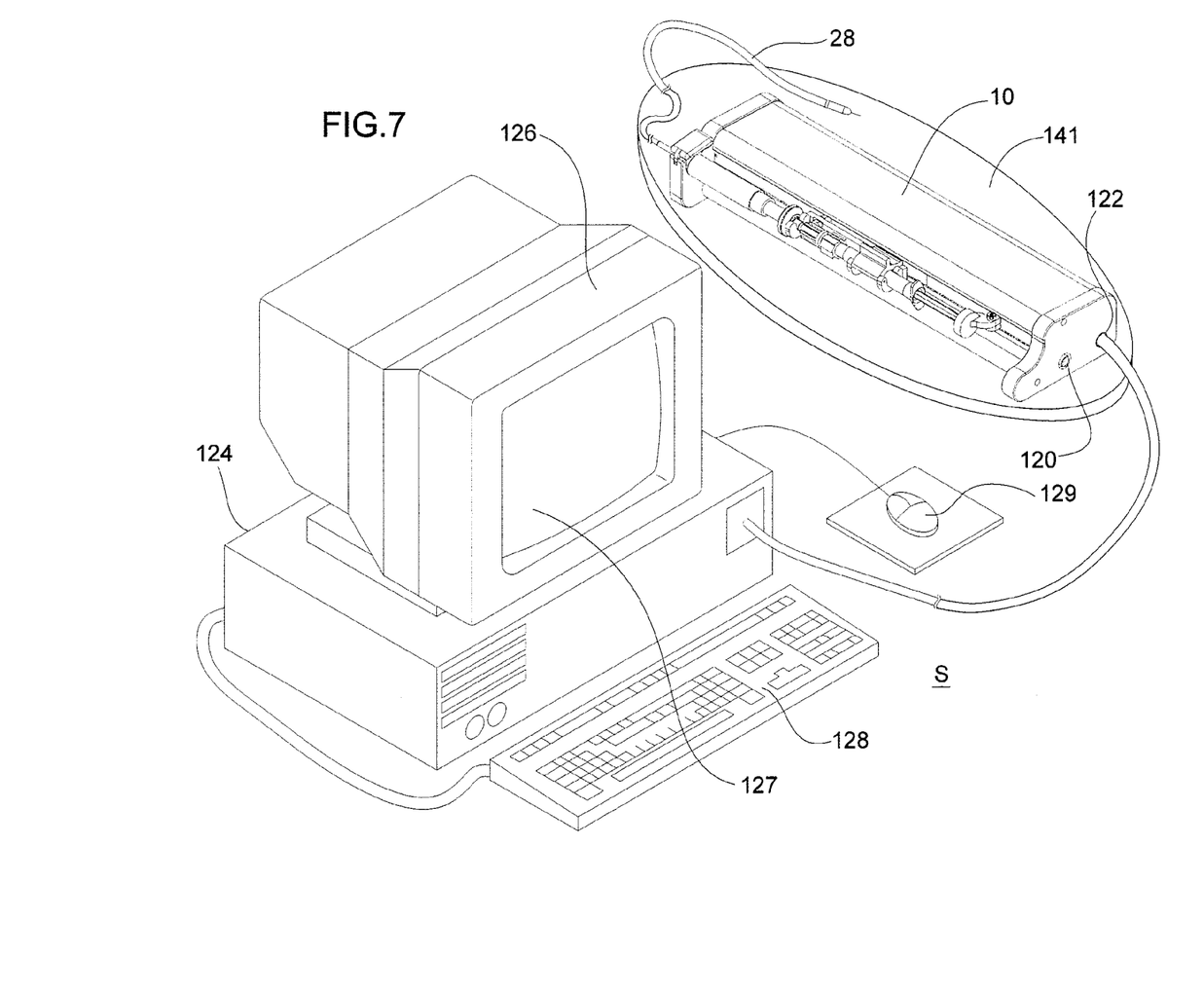
FIG. 7 is a perspective view of an embodiment of a system for automated catheter injection in accordance with the present invention.

Operation of the device 10 is controlled by either a computer program on a stand-alone basis or by remote pendant. The device can also be integrated into a suitable system S, an embodiment of which is illustrated in FIG. 7, for monitoring and displaying the signals received from the electrodes and electromagnetic sensor, such as the system marketed under the trade designation Biosense-NOGA system. Operating within the system S, the device provides a port 120 to receive power and a port 122 for communication with a control computer to relay commands and data to and from the device 10. The circuit board 125 (FIGS. 3 and 5) is mounted on the guide plate 54. The circuit board translates digital commands from a computer to actions and converts analog telemetry from the device to formats suitable for the computer. The computer may include a central processing unit 124, a display 126, and a mouse 129 and keyboard 128 for user input. Alternatively, the mouse and the keyboard may be substituted by a touch-screen 127. It is understood that FIG. 7 does not illustrate all possible or necessary components and communication connections for operation of the catheter 28.

Figure 6:
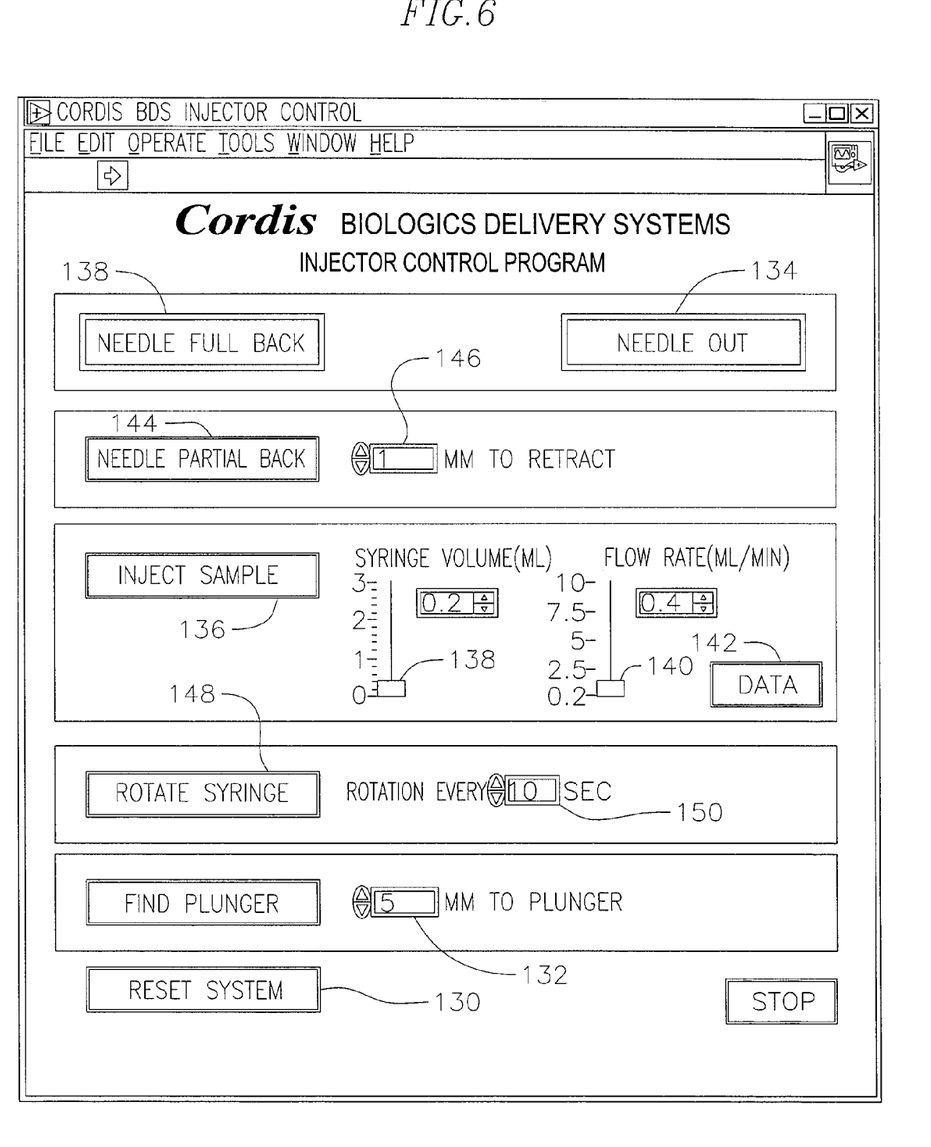
FIG. 6 is screenshot of a graphical user interface according to an embodiment of the invention.

The computer includes a control program, which in one embodiment allows the user to control actions of the device by means of a control program user interface that is displayed on the display. As shown in FIG. 6, a sample interface includes various buttons a user can select. The interface may allow a selection of an initial action of locating a start position of the plunger with a FIND PLUNGER button 130. The button serves to activate the plunger control assembly 22 to move the contact pad distally so as to establish contact with the plunger prior to initiation of an injection procedure. The amount of movement of the assembly 22 is based on the selection the user makes with the MM TO PLUNGER incremental/decremental button 132. The latter could be replaced by a force sensing contact pad that alerts the system when contact with the plunger has been established.

An injection cycle or procedure involves the extension of the needle, depression of the plunger, and retraction of the needle. In that regard, the interface provides a NEEDLE OUT button 134 to extend the needle, an INJECT SAMPLE button 136 to depress the plunger, and a NEEDLE FULL BACK button 138 to retract the needle. Separate buttons are provided because the present invention recognizes the advantages of separating each stage of the injection cycle. One advantage is to allow the user to look for parameters that may suggest a stage should be maintained, discontinued, or repeated before another stage is commenced. For example, prior to selecting the INJECT SAMPLE button, the user may look to various parameters such as voltage criteria (e.g., ECG detection of PVC spike) or stability criteria (e.g., loop stability) that indicate or suggest the needle has penetrated tissue and is in stable contact with the tissue.

Additional buttons for the injection cycle include a SYRINGE VOLUME slider button 138 and a FLOW RATE slider button 140 for the user to, respectively, input the starting volume of injectate in the syringe, and set the injection rate. A typical myocardium revascularization procedure may involve about ten to fifteen instances of injections, each of which uses about 0.2 ml of injectate over about 30 seconds per injection. Thus, a single injector with the syringe carrying a starting injectate volume of at least 3.0 ml should be sufficient to complete most myocardium revascularization procedures. Using the FLOW RATE slider button, a user can select a range of flow rates between about 0.2 ml/min to about 10 ml/min. A DATA button 142 can be selected to recover data regarding force and linear movement of the plunger over time.

The illustrated embodiment also includes a NEEDLE PARTIAL BACK button 144 to retract the needle in stages as set by MM TO RETRACT increment/decrement button 146. Micro-retraction of the needle may be desired in lieu of the NEEDLE FULL BACK button 138 under certain situations, for example, where there is a concern that the needle has penetrated microvasculature or encountered other factors that may cause a washout of the injectate. Slowly retracting the needle may decrease the amount of washout.

The interface of FIG. 6 also provides a ROTATE SYRINGE button 148 to for agitating the injectate. How often the agitation is to occur can be set by a ROTATION EVERY increment/decrement button 150.

It is understood that a user may follow a variety of preparatory procedures before the catheter enters the patient's body, such as depressing the plunger to fill dead space in the syringe. This procedure is crucial for ensuring that the needle lumen of the entire length of the catheter contains no air and is filled entirely with the injectate. Convention injection procedures involve the creation of a 3-D map of the patient's heart beforehand. The mapping may be accomplished with the use of a mapping catheter that is removed prior to insertion of the injection catheter. Alternatively, the injection catheter can have mapping capabilities such that it maps as well as injects. In any case, prior to an injection procedure, the user is provided with a 3-D map of the patient's heart by which he has identified the target site(s).

In one embodiment of the system, operation of the device 10 and system S may be as follows. A user fills the syringe 42 of the injector 26 with injectate, for example, about 3.0 ml. The lumen of the needle is bled to rid the lumen of air. The "throw" adjustment knob 80 is adjusted to set the distance the needle 30 extends beyond the distal end of the catheter 28. The injector 26 is then placed in the device 10 with its distal end in the recess of the distal end cap 16 and the barrel 46 in the proximal pair of brackets 68b and 68c. Care is taken to position the threaded portion 74 in the bracket 68a so that the device has a proper reference location to calibrate injectate dosage and delivery rate. The latches 73 and 75 are secured over the distal end of the piston assembly and the barrel of the syringe.

Power is supplied to the device and system. The program controlling the system is activated and the user interface of FIG. 6 is displayed. The user may first select the ROTATE SYRINGE 148 and set the ROTATION EVERY button 150 so that the injectate does not settle in the barrel of the syringe. He then selects FIND PLUNGER button 130 and establishes contact between the contact pad 92 and the plunger 50 using the MM TO PLUNGER button 132.

It is understood that at some point before the user initiates an injection cycle, the catheter 28 has been placed the patient's body and its distal tip positioned at the target site by means of manual navigation or remote navigation. To initiate an injection cycle, the user selects the NEEDLE OUT button 134. He looks for parameter(s) provided by instruments that may or may not be integrated into the system to indicate tissue penetration and/or contact stability. If he is not satisfied with these parameter(s) and wants to repeat tissue penetration, he can select the NEEDLE FULL BACK button 134 to retract the needle, reposition the catheter tip, and reselect the NEEDLE OUT button 134.

With parameters indicating tissue penetration and stable contact, the user selects the INJECT SAMPLE button 136 to delivery the injectate. It is understood that the user may set the SYRINGE VOLUME button 138 and the FLOW RATE button 140 well before initiation of an injection cycle, but these settings can be changed by use of the buttons 138 and 140 at any time during the injection cycle or operation of the device. In any case, these buttons allow for precise delivery volumes and rates which may translate into greater cell retention and efficacy. To retract the needle and end the injection cycle, the user can select either the NEEDLE FULL BACK button 138 or the NEEDLE PARTIAL BACK button 144 and set the MM TO RETRACT button 146.

The user repeats the above described injection cycle as many times as needed to treat a particular target site. Between each injection cycle, he repositions the catheter tip by manual deflection or external remote navigation.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A device for automating catheter needle injection, comprising:
    a catheter injector having a distal shaft portion and a needle extending through the distal shaft portion, the catheter injector also having a syringe containing injectate, the syringe having a plunger;
    a first actuator adapted to extend a distal end of the needle past a distal end of the distal shaft portion;
    a second actuator adapted to depress the plunger;
    an assembly adapted to agitate the syringe; and
    a force sensor configured to sense pressure indicative of occlusion in the needle.

2. A device of claim 1, wherein the assembly adapted to agitate the syringe includes a member adapted to rotate the syringe.

3. A device of claim 1, further comprising a housing, wherein the first and second actuators and assembly adapted to agitate the syringe are generally situated in the housing.

4. A device of claim 1, wherein the catheter injector and the second actuator are generally aligned in a parallel configuration with each other.

5. A device of claim 1, wherein the first actuator has a movable member and the second actuator and the assembly adapted to agitate the syringe are adapted to move in unison with the movable member.

6. A device of claim 1, wherein the catheter injector further comprises a piston assembly, the first actuator is configured to apply a longitudinal force to the piston assembly and the second actuator is configured to apply a longitudinal force to the plunger.

7. A device of claim 6, wherein the second actuator is configured to apply the longitudinal force to the plunger while the longitudinal force is applied to the piston assembly.

8. A device of claim 1, wherein the assembly adapted to agitate the syringe includes an electric actuator and a rotation assembly responsive to the electric actuator.

9. A device of claim 8, wherein the electric actuator comprises a nitinol wire adapted to change its length when heated by an electric current.

10. A device of claim 1, wherein the first actuator has a movable member and the second actuator is adapted to move with the movable member.

11. A device for use with a catheter injector having a piston assembly and a syringe containing injectate, the syringe having a plunger and a needle, the device comprising:
- a needle control assembly adapted to compress the piston assembly, the needle control assembly comprising a first linear actuator and a movable support member coupled thereto;
- an injection control assembly adapted to depress the plunger, the injection control assembly comprising a second linear actuator and an arm coupled thereto, the arm adapted to act on a distal end of the plunger;
- a force sensor configured to sense pressure indicative of occlusion in the needle;
- an agitator assembly adapted to agitate the injectate in the syringe, the agitator assembly having an electric actuator and a rotation assembly, the rotation assembly having an arm to rotate the syringe;
- a housing configured to enclose at least the needle control assembly, the second linear actuator and the agitator assembly; and
- support members supporting the catheter injector outside of the housing.

12. A device of claim 11, wherein the injection control assembly is adapted to move in unison with the movable support member.

13. A device of claim 11, wherein the catheter injector, the first linear actuator and the second linear actuator are in a generally parallel configuration with each other.

14. A system for automating catheter injection, comprising:
- a device adapted for use with a catheter injector having a piston assembly and a syringe containing injectate, the syringe having a plunger and a needle, comprising:
    - a first actuator assembly adapted to compress the piston assembly, the first actuator assembly comprising a first linear actuator and a movable support member coupled thereto;
    - a second actuator assembly adapted to depress the plunger, the second actuator assembly comprising a second linear actuator and an arm coupled thereto, the arm adapted to act on a distal end of the plunger;
    - an agitator assembly adapted to agitate the injectate in the syringe, the agitator assembly having an electric actuator and a rotation assembly, the rotation assembly having an arm to rotate the syringe; and
    - a force sensor configured to sense pressure indicative of occlusion in the needle; and
- a central processing unit configured to control the first and second actuator assemblies and the agitator assembly.

15. A system of claim 14, further comprising a display to provide visual output to a user.

16. A system of claim 14, further comprising an input device for a user to relay commands and operating parameters to the central processing unit.

\* \* \* \* \*